(12) United States Patent
Yan et al.

(10) Patent No.: US 10,912,479 B2
(45) Date of Patent: Feb. 9, 2021

(54) METHOD FOR ACCURATELY EXTRACTING ABNORMAL POTENTIAL WITHIN QRS

(71) Applicant: Xi'an Jiaotong University, Xi'an (CN)

(72) Inventors: Xiangguo Yan, Xi'an (CN); Ning Wu, Xi'an (CN); Chongxun Zheng, Xi'an (CN); Gang Wang, Xi'an (CN)

(*) Notice: Subject to any disclaimer, the term of this patent is extended or adjusted under 35 U.S.C. 154(b) by 0 days.

(21) Appl. No.: 16/609,174

(22) PCT Filed: Nov. 19, 2018

(86) PCT No.: PCT/CN2018/116214
§ 371 (c)(1),
(2) Date: Oct. 28, 2019

(87) PCT Pub. No.: WO2019/140998
PCT Pub. Date: Jul. 25, 2019

(65) Prior Publication Data
US 2020/0337582 A1    Oct. 29, 2020

(30) Foreign Application Priority Data

Jan. 22, 2018    (CN) .......................... 2018 1 0061071

(51) Int. Cl.
*A61B 5/0472*    (2006.01)
*A61B 5/04*    (2006.01)
(Continued)

(52) U.S. Cl.
CPC ........ *A61B 5/0472* (2013.01); *A61B 5/04014* (2013.01); *A61B 5/04017* (2013.01);
(Continued)

(58) Field of Classification Search
None
See application file for complete search history.

(56) References Cited

U.S. PATENT DOCUMENTS 9,943,244 B2    4/2018   Hopenfeld
2009/0076403 A1    3/2009   Hopenfeld
(Continued)

FOREIGN PATENT DOCUMENTS

CN         1951320 A    4/2007
CN         103705234 A    4/2014
(Continued)

*Primary Examiner* — Kennedy Schaetzle
(74) *Attorney, Agent, or Firm* — Novoclaims Patent Services LLC; Mei Lin Wong

(57) ABSTRACT

A method for accurately extracting an abnormal potential within a QRS, comprising: in an ideal electrocardiographic signal pre-estimation stage, pre-estimating an ideal electrocardiographic signal using a non-linear transformation technology; according to the pre-estimated ideal electrocardiographic signal, further estimating the ideal electrocardiographic signal by using a spline method, so as to accurately estimate the ideal electrocardiographic signal; and according to the accurately estimated ideal electrocardiographic signal, accurately extracting an abnormal potential within the QRS by means of a mobile standard deviation analysis technology. The method can be used not only on an average electrocardiographic signal after multiple superimposition, but also on a single beat electrocardiographic signal.

5 Claims, 10 Drawing Sheets

(51) Int. Cl.
*A61B 5/0452* (2006.01)
*A61B 5/0456* (2006.01)
*A61B 5/0468* (2006.01)
*A61B 5/00* (2006.01)

(52) U.S. Cl.
CPC .......... *A61B 5/0456* (2013.01); *A61B 5/0468* (2013.01); *A61B 5/04525* (2013.01); *A61B 5/7203* (2013.01); *A61B 5/7221* (2013.01)

(56) References Cited

U.S. PATENT DOCUMENTS

| | | | | |
|---|---|---|---|---|
| 2009/0234239 | A1* | 9/2009 | Shani | A61B 5/0456 600/516 |
| 2016/0022164 | A1* | 1/2016 | Brockway | A61B 5/725 600/509 |

FOREIGN PATENT DOCUMENTS

| | | |
|---|---|---|
| CN | 108523881 A | 9/2018 |
| WO | 2016183683 A1 | 11/2016 |
| WO | 2017213533 A1 | 12/2017 |

\* cited by examiner

METHOD FOR ACCURATELY EXTRACTING ABNORMAL POTENTIAL WITHIN QRS

BACKGROUND OF THE PRESENT INVENTION

Field of Invention

The present invention relates to the field of medical signal processing, and more particular to a method for accurately extracting abnormal potential in QRS from ECG signal.

Description of Related Arts

According to statistics, the total number of sudden cardiac deaths (SCD) in China is more than 500,000 per year. On average, 3 people die within 1 hour of onset every minute due to cardiac causes, and the success rate of rescue is less than 1%. Sudden cardiac death has a younger and younger trend significantly. In some patients, sudden deaths often have no obvious aura symptoms, and the body looks healthy. Therefore, early warning of sudden cardiac death is particularly important, but there is currently no effective means of detection.

Numerous studies have shown that electrical conduction delays in localized areas of the heart are an important cause of sudden cardiac death. This conduction delay causes signal reentry, which can lead to severe ventricular arrhythmias. The regional conduction delay can appear as small fluctuations that are not visible or noticeable in the QRS complex of the body-surface electrocardiogram (ECG). These features are often not clearly reflected in conventional electrocardiograms and require the use of high frequency electrocardiograms with higher sampling frequencies. At present, clinically non-invasive detection of abnormal characteristics of this ventricular depolarization process mainly includes: (1) ventricular late potential (VLP) based on signal average electrocardiogram (SAECG), (2) abnormal potential within QRS (AIQPs), (3) Fragmentation QRS wave (fQRS).

Ventricular late potential examination refers to the high-frequency low-amplitude fragmentation potential of the body surface information superimposed ECG at the end of the QRS complex and extending into the ST segment. It reflects the delayed electrical activity of the myocardium in the ischemic region due to slow and irregular reentry activity in the ischemic region of the myocardium. The late potential examination has important value in the prediction of sudden death after acute myocardial infarction.

Clinically, the most widely used method is the time-domain VLP detection method. Although this analysis has a high negative predictive value, the positive predictive effect is not good. The main reason for the low positive predictive rate of the VLP detection method is that only the high frequency low amplitude fragmentation potential at the QRS complex terminal and extended to the ST segment is detected.

A large number of animal myocardial infarction models and human body mapping basic research results clearly indicate that these high-frequency low-amplitude fragmentation potentials are not only present in the terminal region of the QRS complex, but may also be hidden in the QRS complex. In some myocardial infarction sites, the high-frequency low-amplitude fragmentation potential may only exist in the QRS complex and is not reflected in the terminal of the QRS complex. If these high-frequency low-amplitude fragmentation potentials in the QRS complex can be accurately extracted, the reliability of early warning of sudden cardiac death can be significantly improved.

These high-frequency low-amplitude fragmentation potentials in the QRS complex are also called QRS internal abnormal potentials (AIQPs). Extracting AIQPs is a challenging task because AIQPs is embedded in QRS waves and are very weak, and are rapidly changed and unpredictable signals. At present, a variety of methods have been proposed to address this challenge. The autoregressive moving average (ARMA) model of the discrete cosine transform (DCT) domain has been used to estimate AIQPs. The basic idea is to simulate a normal QRS wave with a low-order ARMA model, so that unpredictable AIQPs can be extracted. Some scholars have also proposed to use wavelet transform to analyze the high-frequency components in the QRS wave, and based on this to diagnose malignant ventricular arrhythmia. Many extraction methods use linear models or linear transformation techniques. Since the working mechanism of the human heart is very complicated and fine, modeling the QRS complex into a nonlinear signal may get closer to the actual situation. Some scholars have proposed a method of approximating QRS waves with a radial basis function nonlinear neural network with the same smoothness, and achieved good results. But the main disadvantage is that there are too many parameters that need to be adjusted. The optimal number of neurons varies from person to person. Improper parameter setting will overestimate or underestimate the error of RBF neural network approximation and affect the extraction accuracy.

A large number of studies have shown that AIQPs parameters can significantly improve the diagnostic accuracy for patients with high risk of ventricular arrhythmia, but the extraction accuracy of AIQPs extraction technology still cannot meet the requirements, and the robustness of extraction technology needs to be further improved.

The original ECG signal sampled during the ECG measurement is represented by x(i), which includes the power frequency interference p(i), the baseline drift b(i), the measurement noise n(i), and the abnormal potential in the QRS (AIQPs) to be extracted AIQP(i); the ideal ECG signals without the above components are represented by $X_p(i)$;

$$x(i)=x_p(i)+\text{AIQP}(i)+p(i);+b(i);+n(i), \quad (1)$$

Wherein AIQP(i) is the abnormal potential in the QRS to be extracted in the effective interval of AIQPs, and the other parts take the value of 0.

The signal x(i) after removing power frequency interference and baseline drift is represented by $X_2(1)$.

Using the formula (2), a signal for y(i) containing the abnormal potential and noise interference in the QRS to be extracted can be obtained.

$$y(i)=x_2(i)-x_p(i)=\text{AIQP}(i)+n(i), \quad (2)$$

In the effective interval of AIQPs, when the standard deviation of n(i) is small compared with the standard deviation of y(i), it can be considered that y(i)≈AIQP(I), which is the abnormal potential in the QRS to be extracted. The key to the problem is how to get the ideal ECG signal $X_p(i)$ as accurately as possible, how to determine the effective interval of AIQPs and how to quantitatively evaluate whether the extraction result is credible.

SUMMARY OF THE PRESENT INVENTION

In order to solve the problems in the existing technologies, an object of the present invention is to provide a method for accurately extracting abnormal potential in QRS, which utilizes a non-linear transform prediction technique and the combines with the spline method to obtain an ideal ECG signal which does not contain the internal abnormal potential and other interference components in the QRS, and finally to extract the abnormal potential in QRS.

In order to achieve the above object, the technical solution of the present invention is:

a method of accurately extracting abnormal potential in QRS, which comprises the following steps:

Step 1: Preprocessing the original ECG (electrocardiographic) signal $x_1(i)$ to obtain a pre-processed ECG signal $x_2(i$; when the original ECG signal is a measured single heart beat ECG signal, it is processed by a low-pass filter and a power frequency bandpass filter to eliminate the influence of baseline drift and power frequency interference on the subsequent process; when the original ECG signal is a measured ECG signal containing multiple heart beats, it is processed by the signal averaging technique to eliminate the effects of baseline drift, power frequency interference and measurement noise on subsequent processes.

Step 2: Processing feature point detection of the pre-processed ECG signal $x_2(i)$ to determine feature point position and QRS range, and obtaining an estimated ideal ECG signal by nonlinear transformation. First, processing feature point detection of the pre-processed ECG signal to determine feature point position and QRS range; Secondly, filtering the pre-processed ECG signal obtained after processing step 1 by using two low-pass filters of different filtering frequencies respectively. Then, subtracting the obtained two filtering results to obtain a difference signal, and searching for a first zero-crossing position before and after each feature point position of the difference signal. Then, substituting a time range contained in the first zero-crossing position before and after each feature point position by a low-pass filter filtering result of the higher filter frequency of the above two different filtering frequencies, and substituting other parts by a low-pass filter filtering result of the lower filter frequency of the above two different filtering frequencies to obtain a complex signal. Finally, processing low-pass filtering for the complex signal to obtain an estimated ideal ECG signal.

Step 3: According to the pre-processed ECG signal, the feature point position and the estimated ideal ECG signal, using a spline interpolation technique to obtain an accurate estimated ideal ECG signal. Perform subtraction between the pre-processed ECG signal obtained by the step 1 and the estimated ideal ECG signal obtained by the step 2 to obtain an error signal. Search for a zero-crossing position of the error signal. Then, at the position of the zero-crossing point of the error signal obtained after searching and the position of the feature point obtained by the step 2, take a spline weight as 1, and the others as 0. Finally, according to the estimated ideal ECG signal obtained in step 1 and the obtained spline weight, using cubic smoothing splines to obtain an accurate estimated ideal ECG signal.

Step 4: Perform subtraction between the pre-processed ECG signal obtained by the step 1 and the accurate estimated ideal ECG signal obtained by the step 3 to obtain a subtraction result, filter the subtraction result by a band pass filter to obtain a filtered result. Based on the filtered result and the QRS range obtained in the step 2, obtain an abnormal potential in the QRS by moving the standard deviation analysis technique.

Step 5: Perform credibility evaluation on the obtained abnormal potential in the QRS. Using the standard deviation analysis method, evaluate a credibility of the abnormal potential in the QRS obtained in step 4, determine whether the abnormal potential in the QRS obtained in step 4 is credible, and output the evaluation result.

Wherein the step 2 is specifically as follows:

(1) Using $x_2(i)$ to process ECG feature point detection to obtain the QRS range, a starting position $QRS_b$, an ending position $QRS_e$ and a ECG feature point position p(j), the number of feature points is M, J=1, 2, ..., M. The ECG feature points includes at least a QRS starting point, a QRS ending point, and Q, R, S waveform peak points;

(2) Filtering $x_2(i)$ by a higher frequency low-pass filter to obtain $x_h(i)$, $f_h$ refers to a filter frequency of the low-pass filter, 100 Hz≤$f_h$≤200 Hz;

(3) Filtering $x_2(i)$ by a lower frequency low-pass filter to obtain $x_l(i)$, $f_l$ refers to a filter frequency of the low-pass filter, 40 Hz≤$f_l$≤80 Hz;

(4) calculating the difference signal $x_d(i)$ by formula (3):

$$x_d(i)=x_h(i)-x_l(i), \quad (3)$$

Wherein $x_h(i)$ is a filter result of $x_2(i)$ by the higher frequency low-pass filter, $x_l(i)$ is a filter result of $x_2(i)$ by the lower frequency low-pass filter.

(5) Based on the signal $x_d(i)$, searching the difference signal $x_d(i)$ for each ECG feature point time position p(j), j=1, 2, ..., M, at backward and forward direction respectively to obtain a front and a back first zero crossing point respectively, then obtaining the corresponding time position $p_b(j)$ and $p_f(j)$ respectively;

(6) constructing a point set set(j) according to $p_b(j)$ and $p_f(j)$:

$$\text{set}(J)=\{p_b(j), p_b(j)+1, \ldots, p_f(j)-1, p_f(j)\}, \quad (4)$$

Based on this, construct $\text{Set}_h$:

$$\text{set}_h=\{\text{set}(1), \text{set}(2), \ldots, \text{set}(M)\}, \quad (5)$$

Based on $\text{set}_h$, synthesize a complex signal $x_s(i)$ by formula (6):

$$x_s(i) = \begin{cases} x_h(i), & i \in \text{set}_h \\ x_l(i), & i \notin \text{set}_h \end{cases}, \quad (6)$$

(7) Processing low-pass filtering of $x_s(i)$ to obtain estimated ideal ECG signal $x_3(i)$, $f_3$ refers to a filter frequency of the low-pass filter, 100 Hz≤$f_3$≤200 Hz.

Wherein the step 3 is specifically as follows:

(1) Calculating the error signal $x_e(i)$ by equation (7):

$$x_e(i)=x_2(i)-x_3(i) \quad (7)$$

$x_3(i)$ is the estimated ideal ECG signal;

(2) calculate the spline weight W0 by equation (8):

$$w(i) = \begin{cases} 1, & i \text{ is the zero-crossing point of } p(i) \text{ or } x_e(i) \\ 0, & \text{others} \end{cases}, \quad (8)$$

(3) Based on the estimated ideal ECG signal 1 $x_3(i)$ and the spline weight w(i), using the three-order smooth splines to obtain an accurately estimated ideal ECG signal $x_4(i)$.

Wherein the step 4 is specifically as follows:

(1) calculate the difference signal e(l) by equation (9):

$$e(i)=x_2(i)-x_4(i) \quad (9)$$

$x_4(i)$ is the accurately estimated ideal ECG signal;

(2) Bandpass filter e(i) to obtain a signal y(i) which contains an abnormal potential in the QRS to be extracted, the bandpass filter bandwidth is selected according to specific needs;

(3) calculate a moving window variance MSd(i) for the signal y(i), and calculate MSd(i) by equation (10):

$$msd(i) = \begin{cases} \left[\frac{1}{2k+1}\left(\sum_{j=-k}^{k} y^2(i+j)\right) - \frac{1}{2k+1}\left(\sum_{j=-k}^{j=k} y(i+j)\right)^2\right]^{\frac{1}{2}}, & k \leq i \leq N-k \\ msd(k), & i < k \\ msd(N-k), & i > N-k \end{cases} \quad (10)$$

Wherein a window length is 2k+1, and k ranges from 2 ms~5 ms, and a calculated result of MSd(i) is k=2 ms.

(4) calculate a reference MSD value $ref_{msd}$, define an interval of 100 ms before a starting position $QRS_b$ to $QRS_b$ at the QRS is as a reference interval, first calculate a mean value $ref\_msd_{mean}$ of MSd(i) in the reference interval and a standard deviation $ref\_msd_{std}$, then calculate a $ref_{msd}$ by equation (11):

$$ref_{msd} = ref\_msd_{mean} + \alpha * ref\_msd_{std}, \quad (11)$$

wherein α generally choose to be greater than 2;

(5) determine a starting position $AIQP_b$ of $AIQP_s$ based on $ref_{msd}$, the specific method is: starting a forward search from the QRS starting position $QRS_b$, and stopping the search if a duration of msd (i)>$ref_{msd}$ is greater than or equal to a preset constant m, wherein a position at this time is set as $t_b$, calculate the starting position of $AIQP_b$ of $AIQP_s$ by formula (12):

$$AIQP_b = t_b - m - k, \quad (12)$$

Wherein m is generally 5 ms; if the ending position $QRS_e$ of QRS is searched, then $AIQP_b=0$ and stopping the search.

(6) determine whether $AIQP_b$ is searched, if $AIQP_b$ is equal to 0, then exit and return a failure flag, otherwise continue.

(7) determine an ending position $AIQP_e$ of AIQPs based on $ref_{msd}$, wherein the specific method is: starting a backward search from approximately 50 ms after the QRS ending position $QRS_e$, if a duration of msd (i)>$ref_{msd}$ is greater than or equal to m, stopping the search, and the position at this time is set as $t_e$, calculate the ending position of $AIQP_b$ of AIQPs by formula (13):

$$AIQP_e = t_e + m + k, \quad (13)$$

If the starting position $AIQP_b$ of AIQPs is searched, then $AIQP_e=0$ and stopping the search, determine whether $AIQP_e$ is searched, if $AIQP_e$ is equal to 0, then exit and return a failure flag, otherwise continue.

(8) extract abnormal potential AIQP(i) of QRS, which is calculated according to formula (14):

$$AIQP(i) = \begin{cases} y(i), & AIQP_b \leq i \leq AIQP_e \\ 0, & others \end{cases} \quad (14)$$

Wherein $AIQP_b$ is the starting position of AIQPs obtained by searching, $AIQP_e$ is the ending position of AIQPs obtained by searching.

Wherein the step 5 is specifically as follows:
(1) calculate the standard deviation of the reference interval $ref_{std}$ and the standard deviation of QRS region $QRS_{std}$. $ref_{msd}$ is standard deviation of the reference interval y(i), $QRS_{std}$ is the standard deviation of the y(i) in the interval from the QRS starting position $QRS_b$ to the QRS ending position $QRS_e$.

Determine the credibility of the extraction result, which is calculated by formula (15):

$$credibility = \begin{cases} 1, & QRS_{std} \geq \beta * ref_{std} \text{ or } ref_{std} > 5 \ \mu V \\ 0, & others \end{cases} \quad (15)$$

Wherein β>1, the specific selection can be determined according to the actual situation.

If the credibility is equal to 0, then return a failure flag, otherwise return a success flag and at the same time return the extracted abnormal potential AIQP(i) in the QRS.

The advantageous effect of the present invention:

The present invention provides a method for accurately extracting an abnormal potential in a QRS by using an ideal electrocardiographic signal to process estimation for two times. In the stage of ideal ECG signal estimation, nonlinear transformation technology can be used to effectively track the trend of non-ECG feature point regions, and it can effectively eliminate the possible impact of ECG feature points on extracting ideal ECG signals. Based on the estimated ideal ECG signal, the spline method is used to further estimate the ideal ECG signal, and the ideal ECG signal can be accurately estimated. Compared with the prior methods, the method of the invention requires fewer parameters to be selected, and the result is more reliable. The present invention also evaluates the reliability of the extracted abnormal potential in the QRS, thereby ensuring the reliability of the results of application development using the method of the present invention. Compared with the traditional multiple-stack averaging method, a prominent feature of the method of the present invention is that the single-pulse electrocardiographic signal can be extracted in the QRS, which can greatly expand the application range of the AIQPs analysis technology.

The scenarios and scopes applicable to the method of the present invention include: 1) integrating the method of the present invention in an electrocardiograph device to assess the risk of sudden cardiac death in patients during routine electrocardiographic measurements; 2) Integrating the method of the present invention in a conventional multi-parameter monitor for real-time dynamic tracking and monitoring of changes in the condition of patients with myocardial infarction; 3) developing portable or wearable devices that are easy to use to achieve early warning of sudden cardiac death in a family environment; 4) Integrating the method of the present invention in mobile devices (such as mobile phones) can provide a quick and efficient warning method for sudden death risk of the device user.

DETAILED DESCRIPTION OF THE PREFERRED EMBODIMENT

The principles the present invention are described in detail below with reference to the accompanying drawings.

Figure 1:
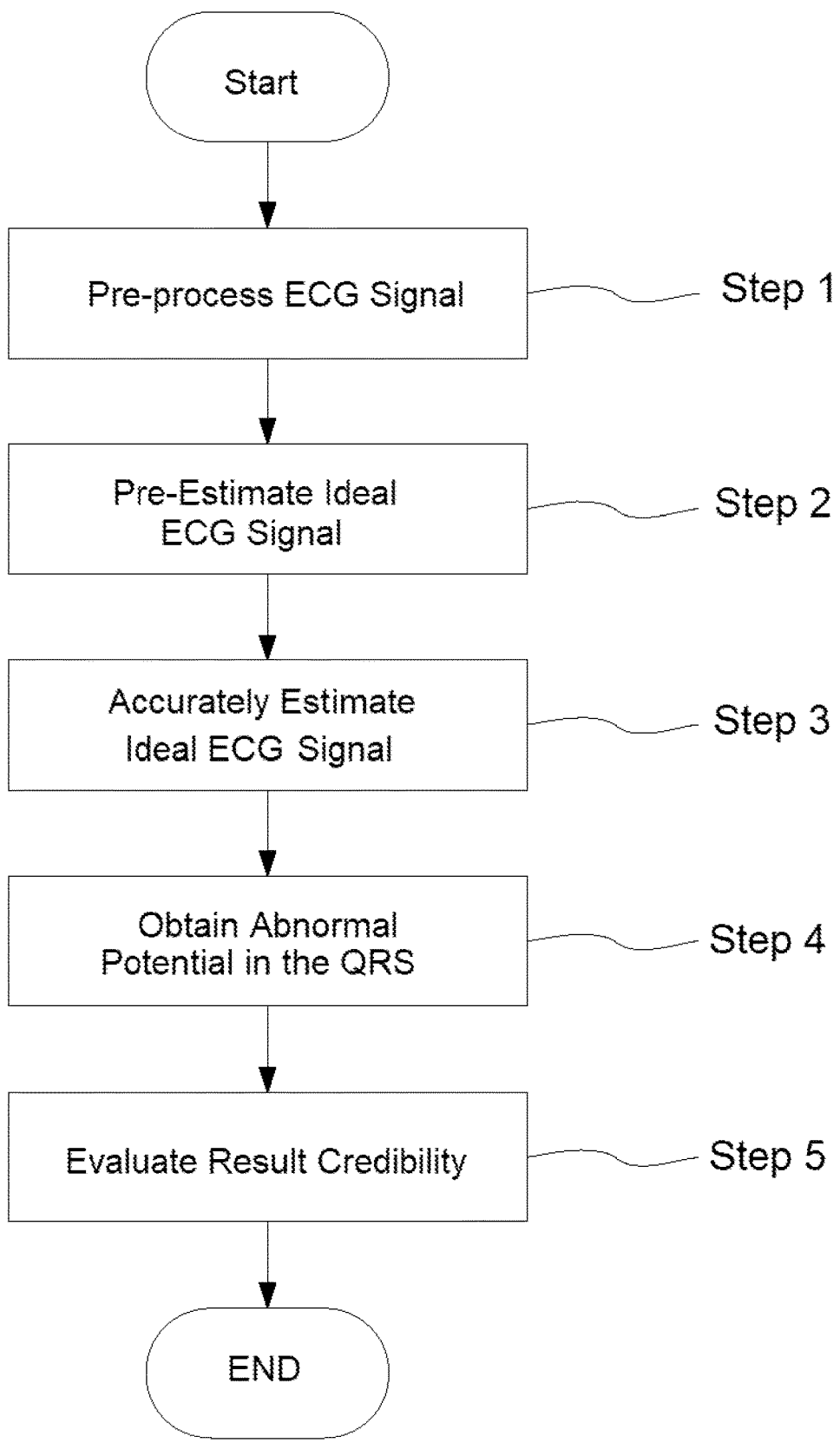
FIG. 1 illustrates a flow chart of the present invention.

Referring to FIG. 1 of the drawings, which is a flowchart of the present invention, illustrates a method for accurately extracting abnormal potential in QRS, comprising the steps of:

Step 1: Preprocessing the original ECG (electrocardiographic) signal $x_1(i)$ to obtain a pre-processed ECG signal $x_2(i)$; when the original ECG signal is a measured single heart beat ECG signal, it is processed by a low-pass filter and a power frequency bandpass filter to eliminate the influence of baseline drift and power frequency interference on the subsequent process; when the original ECG signal is a measured ECG signal containing multiple heart beats, it is processed by the signal averaging technique to eliminate the effects of baseline drift, power frequency interference and measurement noise on subsequent processes.

Step 2: Processing feature point detection of the pre-processed ECG signal $x_2(i)$ to determine feature point position and QRS range, and obtaining an estimated ideal ECG signal by nonlinear transformation. First, processing feature point detection of the pre-processed ECG signal to determine feature point position and QRS range; Secondly, filtering the pre-processed ECG signal obtained after processing step 1 by using two low-pass filters of different filtering frequencies respectively. Then, subtracting the obtained two filtering results to obtain a difference signal, and searching for a first zero-crossing position before and after each feature point position of the difference signal. Then, substituting a time range contained in the first zero-crossing position before and after each feature point position by a low-pass filter filtering result of the higher filter frequency of the above two different filtering frequencies, and substituting other parts by a low-pass filter filtering result of the lower filter frequency of the above two different filtering frequencies to obtain a complex signal. Finally, processing low-pass filtering for the complex signal to obtain an estimated ideal ECG signal.

Step 3: According to the pre-processed ECG signal, the feature point position and the estimated ideal ECG signal, using a spline interpolation technique to obtain an accurate estimated ideal ECG signal. Perform subtraction between the pre-processed ECG signal obtained by the step 1 and the estimated ideal ECG signal obtained by the step 2 to obtain an error signal. Search for a zero-crossing position of the error signal.

Then, at the position of the zero-crossing point of the error signal obtained after searching and the position of the feature point obtained by the step 2, take a spline weight as 1, and the others as 0. Finally, according to the estimated ideal ECG signal obtained in step 1 and the obtained spline weight, using cubic smoothing splines to obtain an accurate estimated ideal ECG signal.

Step 4: Perform subtraction between the pre-processed ECG signal obtained by the step 1 and the estimated ideal ECG signal obtained by the step 3 to obtain a subtraction result, filter the subtraction result by a band pass filter to obtain a filtered result. Based on the filtered result and the QRS range obtained in the step 2, obtain an abnormal potential in the QRS by moving the standard deviation analysis technique.

Step 5: Perform credibility evaluation on the obtained abnormal potential in the QRS. Using the standard deviation analysis method, evaluate a credibility of the abnormal potential in the QRS obtained in step 4, determine whether the abnormal potential in the QRS obtained in step 4 is credible, and output the evaluation result.

Figure 2:
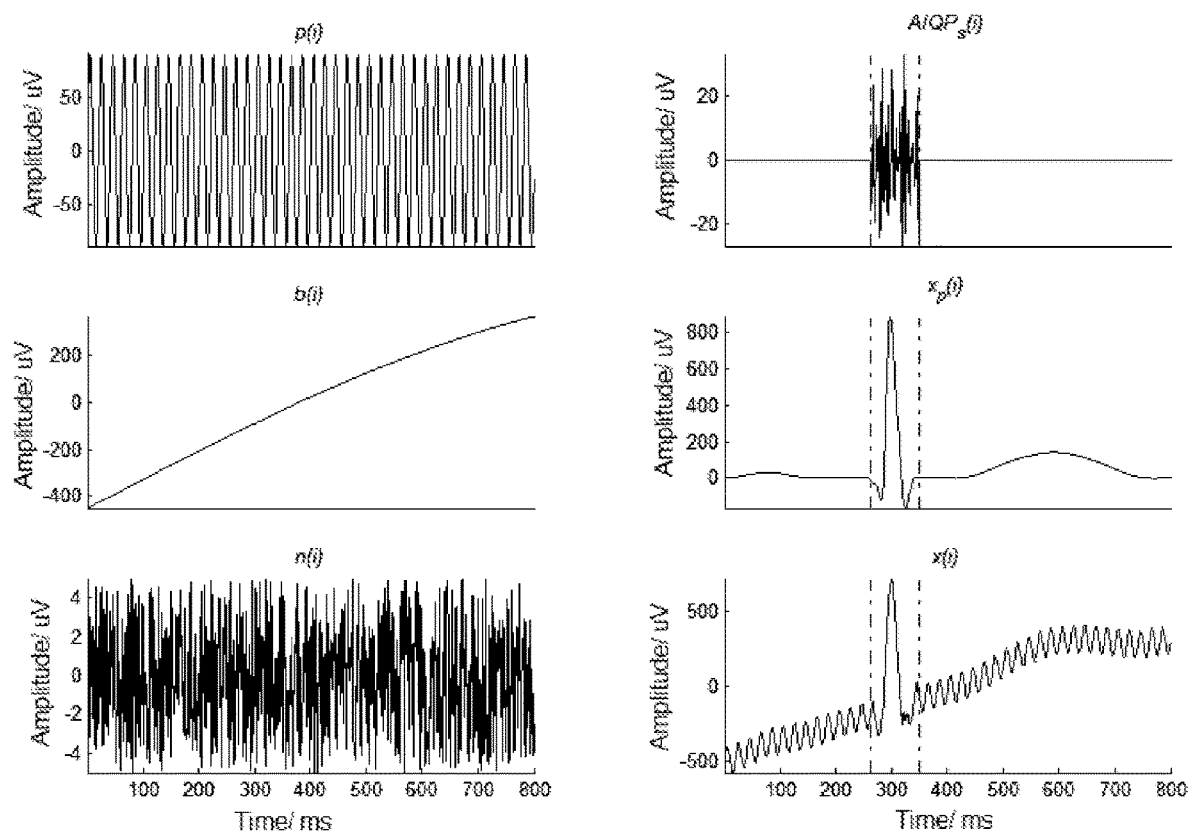
FIG. 2 illustrates is the simulation signal used in the description of the principles of the present invention.

FIG. 2 is an illustration of a simulation of ECG signal $x(i)$ which includes the ideal ECG signal $x_p(i)$, a simulation containing the abnormal potential in the QRS $AIQP_s(i)$ to be extracted, and a power frequency interference $p(i)$, baseline shift $b(i)$ and measurement noise $n(i)$, with a sampling rate is 1000 Hz and a data length N=800 for use in the principles of the present invention.

The step 1, specifically, is as follows: referring to FIG. 3 and FIG. 4, in FIG. 3, 101 refers to remove baseline shift. Use a baseline shift cancellation method to remove the baseline shift. After removing, obtain a signal $x_1(i)$.

At present, there are many baseline drift elimination methods. Since the baseline drift has no significant effect on the final extraction result, in FIG. 4, $x_1(i)$ is obtained by designing the low-pass filter parameters by using a third-order, 1 Hz Butterworth digital filter, and then processing bidirectional zero phase filtering for $x(i)$.

Figure 3:
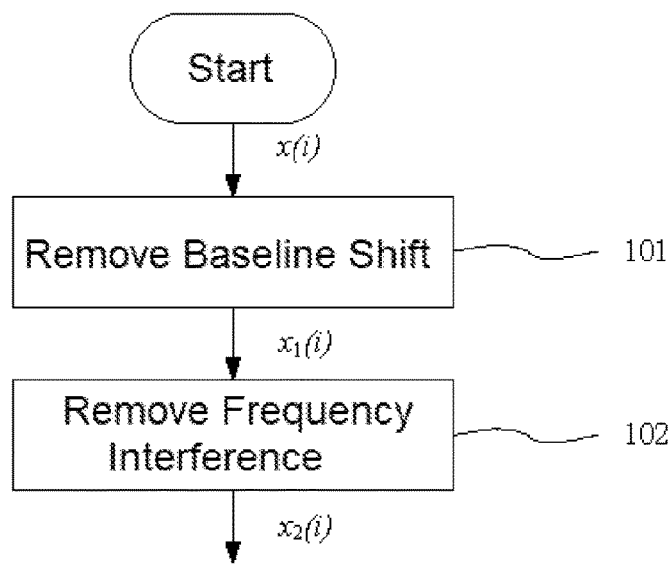
FIG. 3 illustrates a pre-processing flow chart according to an embodiment of the present invention.
Figure 4:
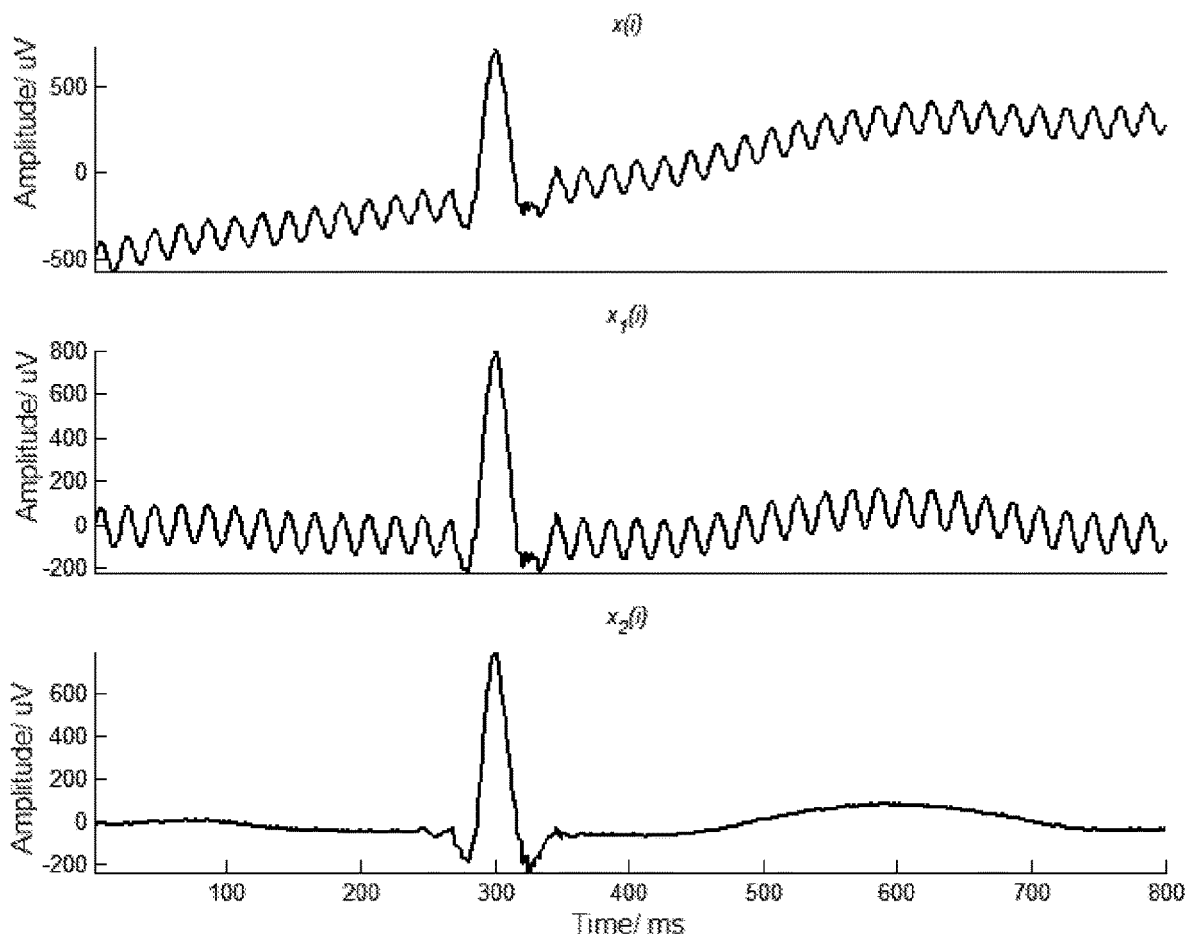
FIG. 4 is a schematic diagram of baseline drift elimination and power frequency interference removal process according to an embodiment of the present invention.

In FIG. 3, 102 refers to remove power frequency interference. Based on the obtained signal $x_1(i)$, use a digital power frequency notch filter to obtain the signal $x_2(i)$ after removing the power frequency interference and the baseline drift. In FIG. 4, $x_2(i)$ is the result obtained by using the digital power frequency notch filter.

Figure 5:
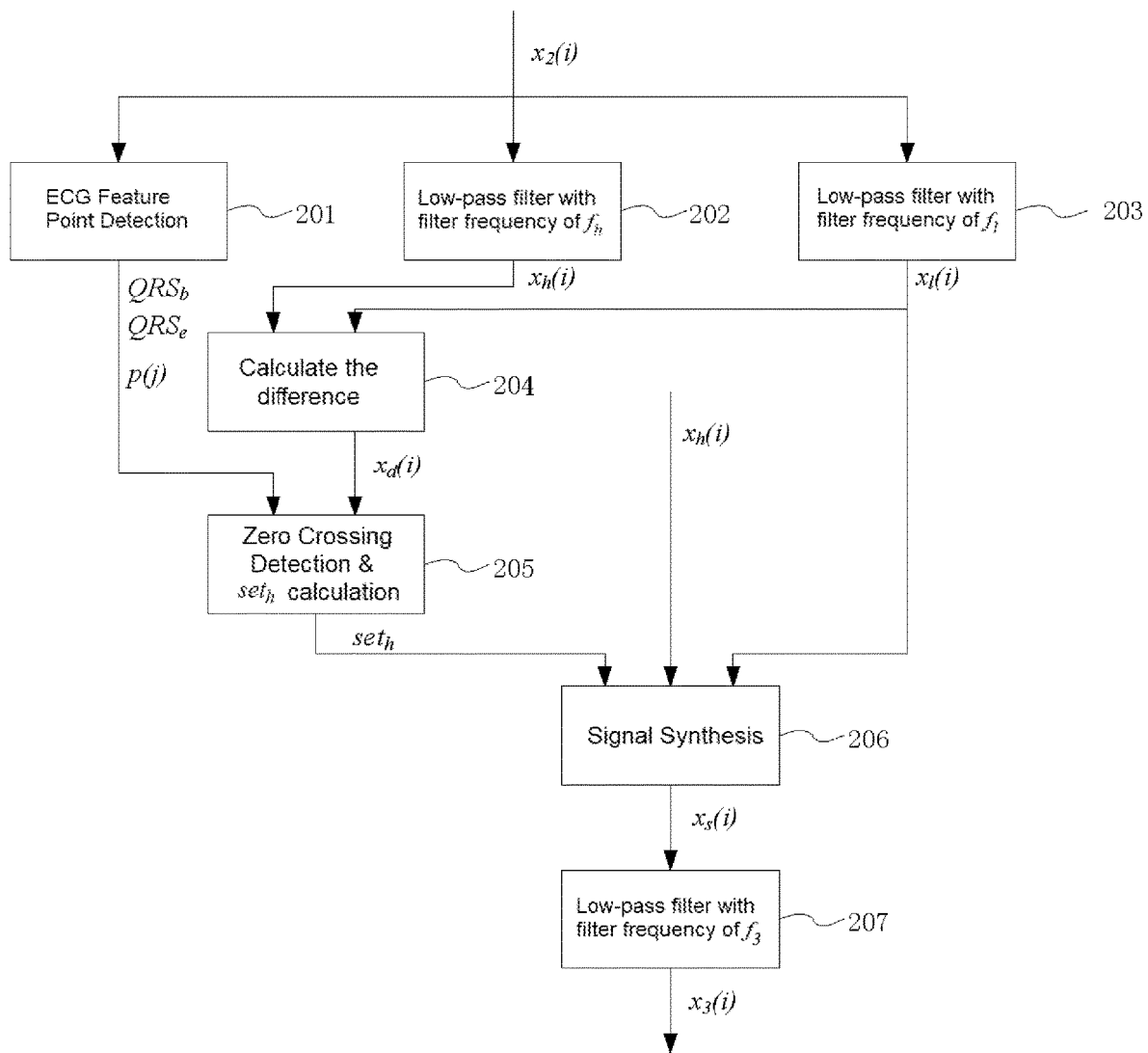
FIG. 5 illustrates a flow chart for estimated ideal ECG signal according to an embodiment of the present invention.
Figure 6:
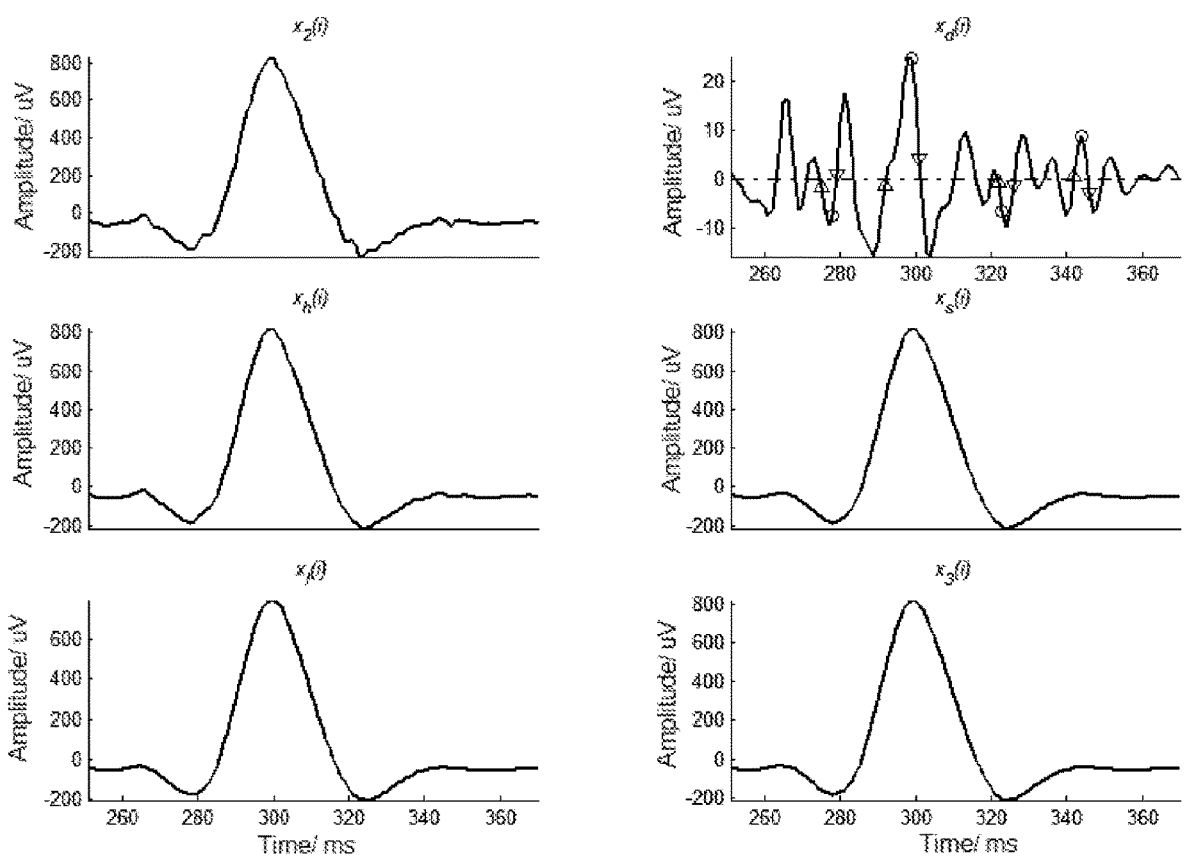
FIG. 6 is a schematic diagram to show a process to obtain the estimated ideal ECG signal according to an embodiment of the present invention.

The step 2, specifically, is as follows: Refer to FIG. 5 and FIG. 6, wherein FIG. 6 is a partial view of the vicinity of the QRS interval. In FIG. 5, 201 refers to a feature point detection algorithm. Using $x_2(i)$ to process ECG feature point detection to obtain the QRS range (starting position $QRS_b$, ending position $QRS_e$) and ECG feature point position $p(j)$, the number of feature points is M, J=1, 2, . . . , M. The ECG feature points at least includes a QRS starting point, a QRS ending point, and Q, R, S waveform peak points.

In FIG. 5, 202 refers to a low-pass filter. Filter $x_2(i)$ by a higher frequency low-pass filter to obtain $x_h(i)$, $f_h$ refers to a filter frequency of the low-pass filter 202, 100 Hz≤200≤Hz. In FIG. 6, $x_h(i)$ is obtained by designing the low-pass filter parameters by using a third-order, $f_h$=150 Hz Butterworth digital filter, and then processing bidirectional zero phase filtering for $x_2(i)$.

In FIG. 5, 203 refers to a low-pass filter. Filter $x_2(i)$ by a lower frequency low-pass filter to obtain $x_1(i)$, $f_l$ refers to a filter frequency of the low-pass filter 203, 40 Hz≤$f_l$≤80 Hz. In FIG. 6, $x_l(i)$ is obtained by designing the low-pass filter parameters by using a third-order, $f_l$=60 Hz Butterworth digital filter, and then processing bidirectional zero phase filtering for $X_2(i)$.

In FIG. 5, 204 refers to a signal subtraction operation. Use equation (3) to calculate the difference signal $x_d(i)$:

$$x_d(i)=x_h(i)-x_l(i), \quad (3)$$

In FIG. 6, $x_d(i)$ is the result after signal subtraction.

In FIG. 5, 205 refers to a zero-crossing detection and a set $set_h$ calculation. Based on the signal $x_d(i)$, search the difference signal $x_d(i)$ for each ECG feature point time position p(j), j=1, 2, . . . , M, at backward and forward direction respectively to obtain a front and a back first zero crossing point respectively, then obtaining the corresponding time position $p_b(i)$ and pf0) respectively.

In FIG. 6, in the $x_d(i)$, the dashed line is a zero-valued line, the symbol "O" represents the point of the time position p(j) corresponding to $x_d(i)$, and the symbols "Δ" and "∇" represent the points of the time position $p_b(i)$ and $p_f(i)$ correspond to $x_d(i)$ respectively, M=4. Since $x_d(i)$ is a time-discrete signal, the actual value corresponding to $x_d(i)$ zero crossing is not necessarily zero.

For each p(j), the point set set(J) is constructed according to $p_b(j)$ and $p_f(j)$:

$$set(j)=\{p_b(j), p_b(j)+1, p_f(j)-1, p_f(j)\}, \quad (4)$$

Based on this, construct $Set_h$:

$$set_h=\{set(1), set(2), \ldots, set(M)\}, \quad (5)$$

In FIG. 5, 206 refers to signal synthesis. Based on $set_h$, the complex signal $x_s(i)$ is synthesized by the formula (6), $$x_s(i) = \begin{cases} x_h(i), & i \in set_h \\ x_l(i), & i \notin set_h \end{cases}, \quad (6)$$

In FIG. 6, $x_s(i)$ refers to the obtained complex signal.

In FIG. 5, 207 refers to a low-pass filter.

Filter $x_s(i)$ to obtain estimated ideal ECG signal $x_3(i)$, $f_3$ refers to a filter frequency of the low-pass filter 207, 100 Hz≤$f_3$≤200 Hz. In FIG. 6, $x_3(i)$ is the estimated ideal ECG signal obtained by designing the low-pass filter parameters by using a third-order, $f_3$=150 Hz Butterworth digital filter, and then processing bidirectional zero phase filtering for $x_s(i)$.

Figure 7:
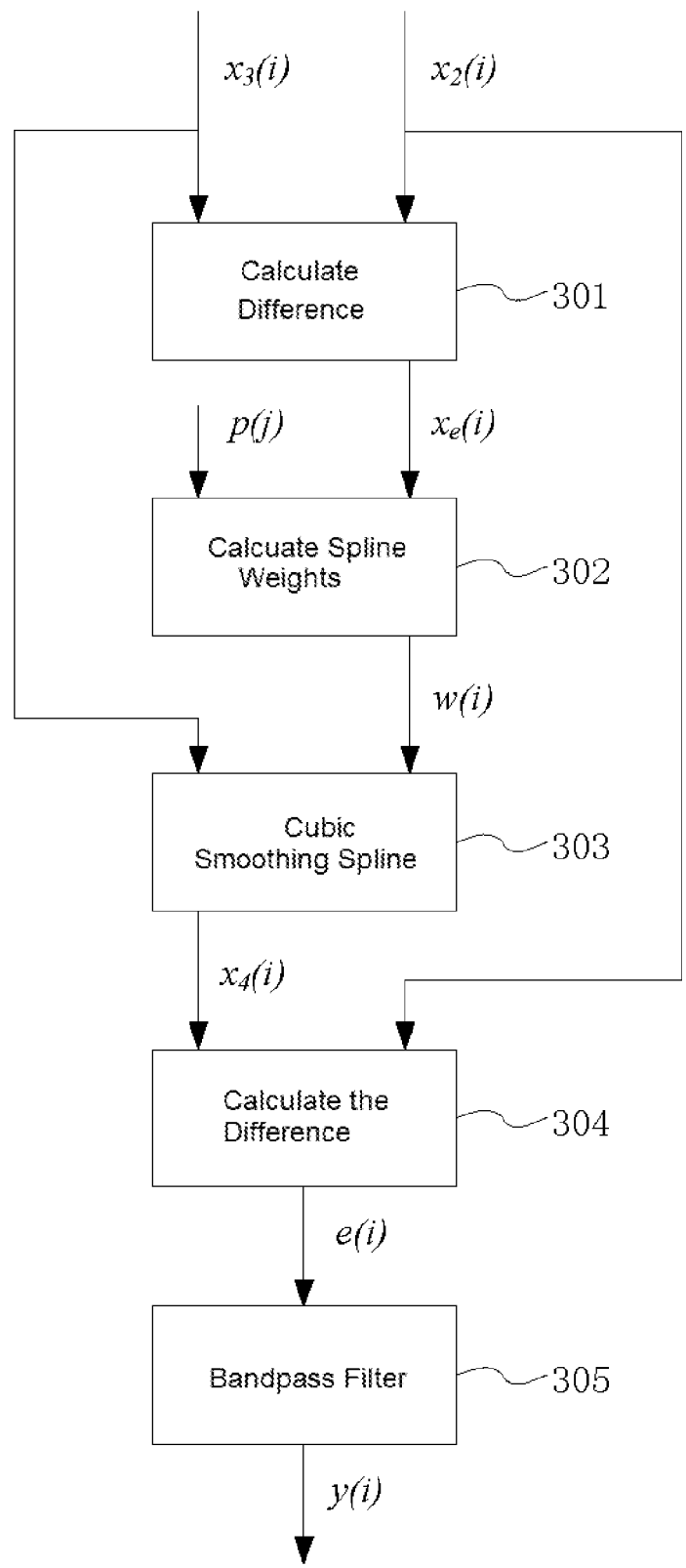
FIG. 7 illustrates a flow chart showing an accurately estimate of ideal ECG signal according to an embodiment of the present invention.
Figure 8:
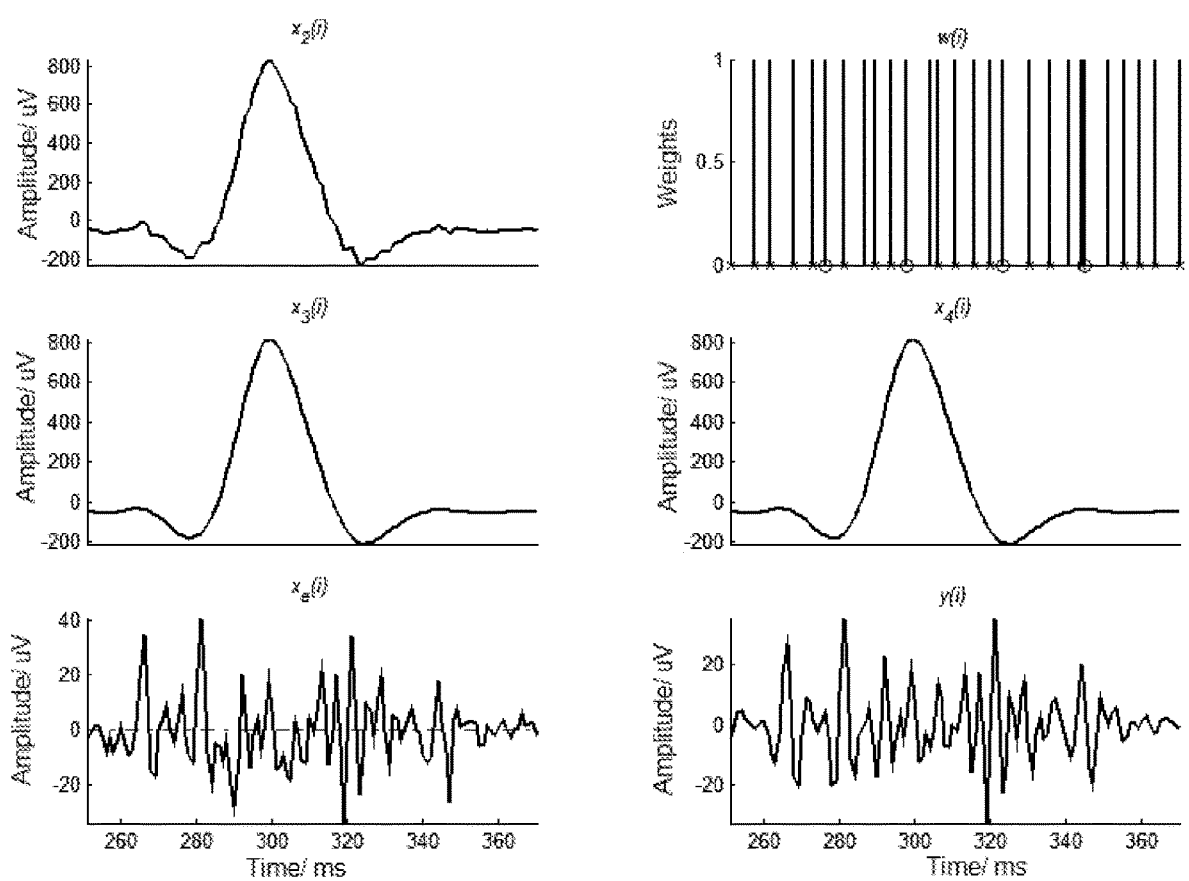
FIG. 8 is a schematic diagram to show a process for accurately estimating the ideal ECG signal by using a cubic smooth spline according to an embodiment of the present invention.

The step 3, specifically, is as follows: Refer to FIG. 7 and FIG. 8, wherein FIG. 8 is a partial view of the vicinity of the QRS interval. In FIG. 7, 301 refers to a signal subtraction operation. Use equation (7) to calculate the error signal $x_e(i)$:

$$x_e(i)=x_2(i)-x_3(i), \quad (7)$$

In FIG. 8, $x_e(i)$ is the result after signal subtraction.

In FIG. 7, 302 refers to the calculated spline weight. Use equation (8) to calculate the spline weight w(i):

$$w(i) = \begin{cases} 1, & i \text{ is the zero-crossing point of } p(i) \text{ or } x_e(i) \\ 0, & \text{others} \end{cases}, \quad (8)$$

In FIG. 8, w(i) is the spline weight obtained by using equation (7).

In FIG. 7, 303 refers to the cubic smoothing spline operation. Based on the estimated ideal ECG signal 1 $x_3(i)$ and the spline weight w(i), use the three-order smooth splines to obtain an accurately estimate result for the ideal ECG signal $x_4(i)$.

In FIG. 8, $x_4(i)$ is the accurately estimate result for the ideal ECG signal obtained.

The step 4, specifically, is as follows: Refer to FIG. 7, FIG. 9 and FIGS. 8 and 10.

In FIG. 7, 304 refers to a signal subtraction operation. Use equation (9) to calculate the difference signal e(i):

$$e(i)=x_2(i)-x_4(i), \quad (9)$$

In FIG. 7, 305 refers to a band pass filter. Band pass filter e (i) to obtain a signal y(i) which contains an abnormal potential in the QRS to be extracted, $f_1$ and $f_2$ refer to a low frequency and a high frequency of the band pass filter, $f_1$ and $f_2$ can be selected based on the specific subsequent applications. In FIG. 8, y(i) is obtained by designing the band pass filter parameters by using a fifth-order, $f_1$=70 Hz, $f_2$=300 Hz, Butterworth digital filter, and then processing bidirectional zero phase filtering.

Figure 9:
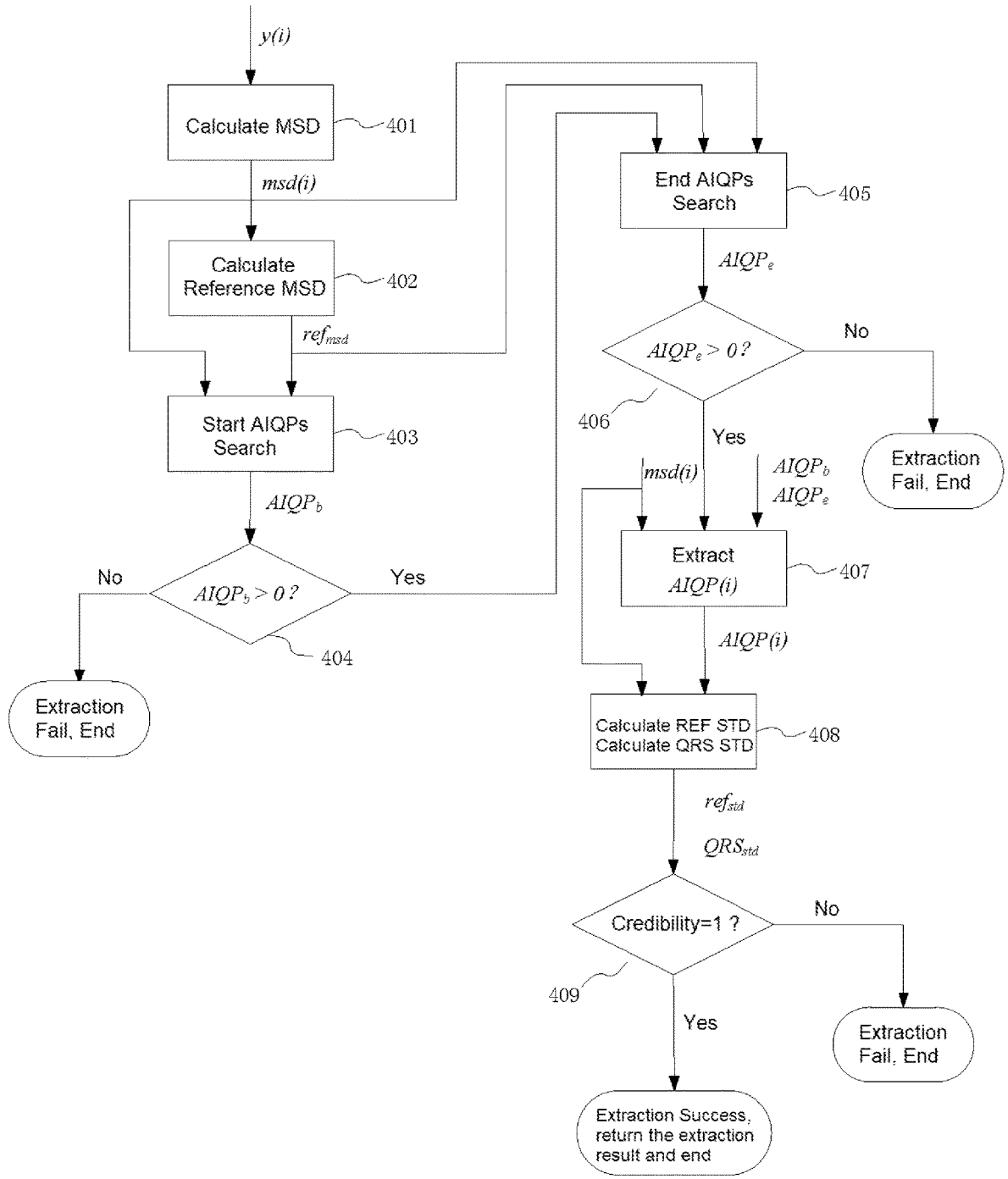
FIG. 9 illustrates a flow chart of extracting abnormal potential in QRS and evaluating the result credibility.

In FIG. 9, 401 refers to the calculation of the moving window variance msd(i) for the signal y(i). Use equation (10) to calculate msd(i):

$$msd(i) = \begin{cases} \left(\frac{1}{2k+1}\left(\sum_{j=-k}^{k} y^2(i+j) - \frac{1}{2k+1}\left(\sum_{j=-k}^{j=k} y(i+j)\right)^2\right)\right)^{\frac{1}{2}}, & k \le i \le N-k \\ msd(k), & i < k \\ msd(N-k), & i > N-k \end{cases}, \quad (10)$$

Wherein the window length is 2k+1, and k generally ranges from 2 ms~5 ms.

Figure 10:
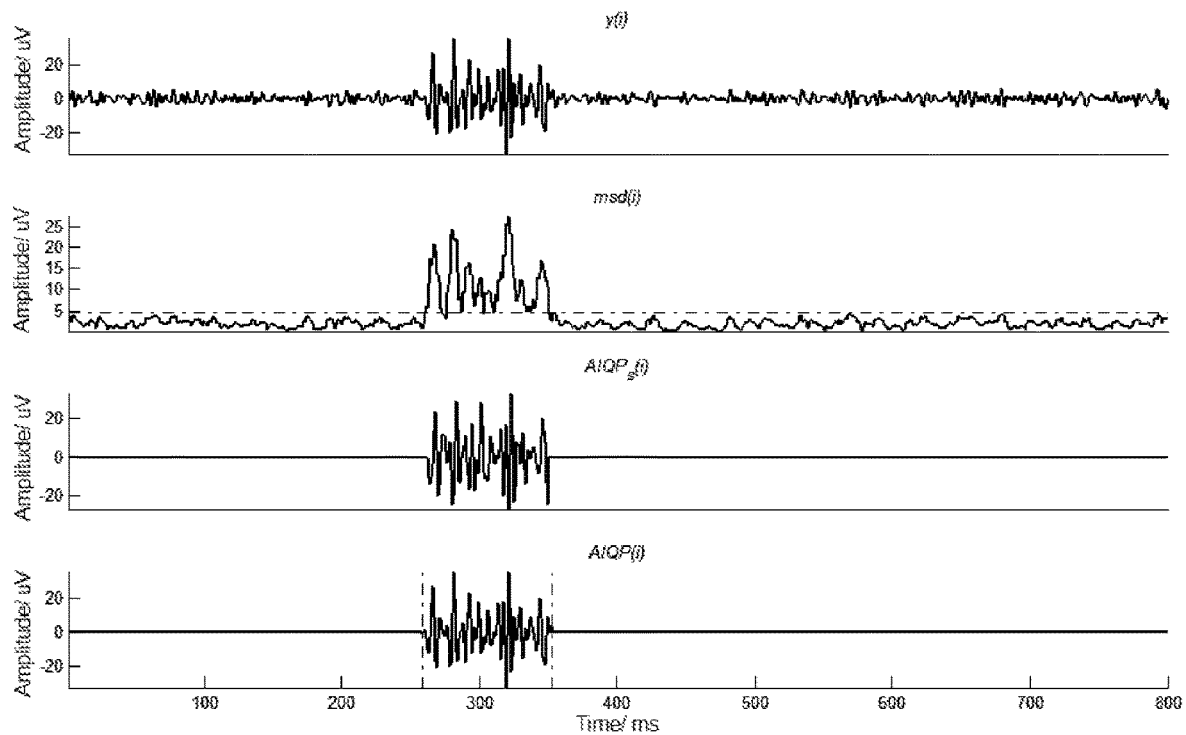
FIG. 10 illustrates a schematic process of extracting abnormal potential in QRS and evaluating the result credibility.

In FIG. 10, the calculated result of msd(i) is k=2 ms.

In FIG. 9, 402 refers to the calculation reference MSD value $ref_{msd}$. The interval of approximately 100 ms before a starting position $QRS_b$ to $QRS_b$ at the QRS is defined as a reference interval. First calculate the mean value $ref\_msd_{mean}$ of MSd(i) in the reference interval and the standard deviation $ref\_msd_{std}$, then calculate the $ref_{msd}$ by equation (11):

$$ref_{msd}=ref\_msd_{mean}+\alpha*ref\_msd_{std}, \quad (11)$$

wherein α generally choose to be greater than 2, the specific choice can be determined according to the actual situation.

In FIG. 10, the amplitude value of the horizontal dashed line in msd(i) represents the value of $ref_{msd}$, α=3.

In FIG. 9, 403 refers to the determination of the starting position $AIQP_b$ of AIQPs based on $ref_{msd}$. The specific method is: starting a forward search from the QRS starting position $QRS_b$. If a duration of msd (i)>$ref_{msd}$ is greater than or equal to m, stopping the search, and the position at this time is set as $t_b$, the starting position of $AIQP_b$ of AIQPs is calculated according to formula (12):

$$AIQP_b=t_{b-m-k}, \quad (12)$$

Wherein M is generally 5 ms; if the ending position $QRS_e$ of QRS is searched, then $AIQP_b$=0 and stopping the search.

In FIG. 10, 404 refers to the determination of whether $AIQP_b$ is searched. If $AIQP_b$ is equal to 0, then exit and return a failure flag, otherwise continue.

In FIG. 9, 405 refers to the determination of the ending position $AIQP_e$ of AIQPs based on $ref_{msd}$. The specific method is: starting a backward search from approximately 50 ms after the QRS ending position $QRS_e$. If a duration of $msd(i) > ref_{msd}$ is greater than or equal to 111, stopping the search, and the position at this time is set as $t_e$, the ending position of $AIQP_b$ of AIQPs is calculated according to formula (13):

$$AIQP_e = t_{e+m+k}, \quad (13)$$

If the starting position $AIQP_b$ of AIQPs is searched, then $AIQP_e = 0$ and stopping the search.

In FIG. 9, 406 refers to the determination of whether $AIQP_e$ is searched. If $AIQP_e$ is equal to 0, then exit and return a failure flag, otherwise continue.

In FIG. 9, 407 refers to the extraction of abnormal potential AIQP(i) of QRS, which is calculated according to formula (14):

$$AIQP(i) = \begin{cases} y(i), & AIQP_b \le i \le AIQP_e \\ 0, & others \end{cases}, \quad (14)$$

In FIG. 10, AIQP(i) is the extracted abnormal potential AIQPs in QRS, wherein the two vertical dashed lines represent $AIQP_b$ and $AIQP_e$ respectively.

The step 5, specifically, is as follows: Refer to FIG. 9 and FIG. 10. In FIG. 9, 408 refers to the standard deviation of the calculated reference interval $ref_{msd}$ and the standard deviation of QRS region $QRS_{std}$. $ref_{msd}$ is standard deviation of the reference interval y(i), $QRS_{std}$ is the standard deviation of the y(i) in the interval from the QRS starting position $QRS_b$ to the QRS ending position $QRS_e$.

In FIG. 9, 409 is the credibility judgment of the extraction result, and the credibility is calculated according to formula (15).

$$credibility = \begin{cases} 1, & QRS_{std} \ge \beta * ref_{std} \text{ or } ref_{std} > 5 \ \mu V \\ 0, & others \end{cases}, \quad (15)$$

Wherein $\beta > 1$ the specific selection can be determined according to the actual situation.

If the credibility is equal to 0, then return a failure flag, otherwise return a success flag and at the same time return the extracted abnormal potential AIQP(i) in the QRS.

Figure 11:
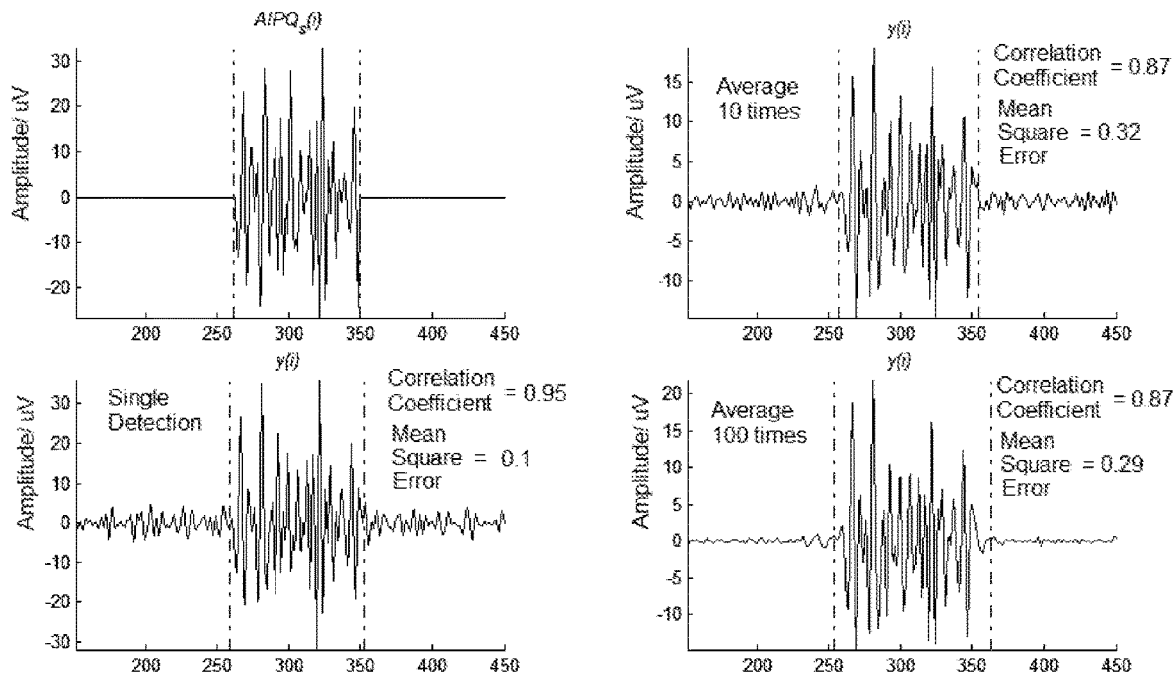
FIG. 11 is a graph showing the results of the abnormal potential extraction in the QRS by the method of the present invention for a single beat ECG and a superimposition average of multiple beat ECG.

FIG. 11 illustrates a method of generating simulation signal according to the description of the present invention. The simulated heart beat ECG is generated 1 time, 10 times, and 100 times respectively, and then superimpose and average the multiple simulated heartbeat ECGs, for the obtained 1 time heart beat ECG, and the simulated heart beat average ECG of 10 times and 100 times ECGs, extract AIQP(i) by the method of the present invention respectively. The extracted AIQP(i) of the 1 time heart beat ECG, and the simulated heart beat average ECG of 10 times and 100 times ECGs is compared with the simulated AIQP(i) to be extracted, the correlation coefficient and mean square error are: 0.95, 0.1; 0.87, 0.32; 0.87, 0.29. The results show that the method of the present invention only requires a single heart beat ECG to extract AIQP(i). Compared with multiple superimposed averages, the AIQP(i) extracted by single heart beat ECG is more accurate when the measurement noise is small. It can also be seen from FIG. 11 that as the average number of superpositions increases, the interference of the reference interval in step 4 of the present invention becomes smaller and smaller. Therefore, if the signal interference of ECG obtained by detection is relatively great, which causes extraction failure for single heartbeat ECG, then extraction by superimposing and averaging the multiple heartbeat ECG can be processed.

Figure 12:
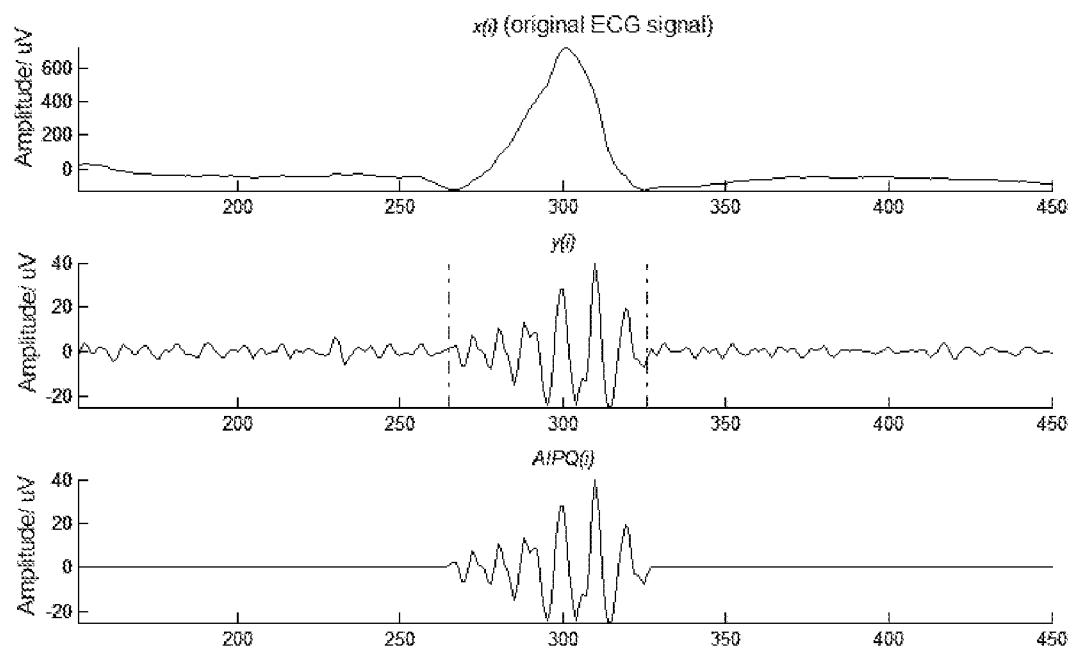
FIG. 12 is a graph showing the results of QRS internal abnormal potential extraction of a single beat ECG of a patient with myocardial infarction by the method of the present invention.
Figure 13:
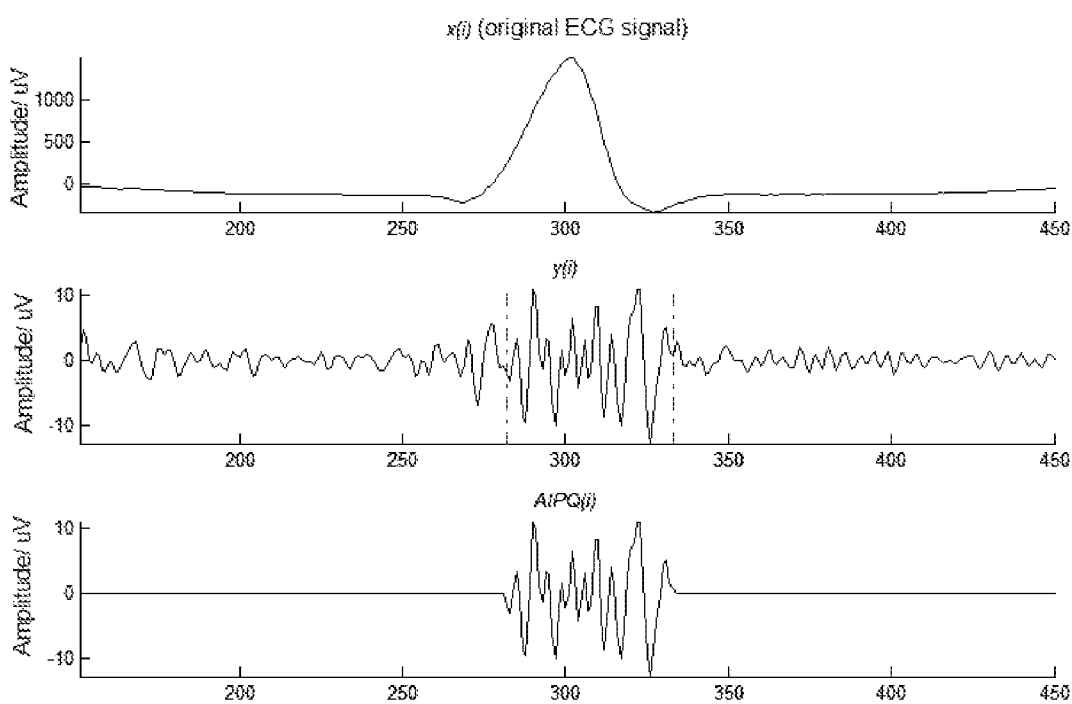
FIG. 13 is a graph showing the results of extracting abnormal potentials in QRS of a single beat ECG of a healthy person by the method of the present invention.

FIG. 12 is a result of AIQP(i) extraction of a single heart beat ECG of a patient with myocardial infarction by the method of the present invention, and FIG. 13 a result of AIQP(i) extraction of a single heart beat ECG of a heart healthy person by the method of the present invention. The result of AIQP(i) extraction. Comparing FIG. 12 and FIG. 13, it can be found that the amplitude of AIQP(i) in patients with myocardial infarction is significantly larger than that in healthy subjects, and the morphology of both AIQP(i) is also significantly different. These features can be used for early warning of sudden cardiac death.

What is claimed is:

1. A method of accurately extracting abnormal potential in QRS, comprising the steps of:

Step 1: Pre-processing an original electrocardiographic (ECG) signal $x_1(i)$ to obtain a pre-processed ECG signal $x_2(i)$; when the original ECG signal is a measured single heart beat ECG signal, processing it by a low-pass filter and a power frequency bandpass filter to eliminate an influence of baseline drift and power frequency interference on subsequent processing; when the original ECG signal is a measured ECG signal containing multiple heart beats, processing it by a signal averaging technique to eliminate effects of baseline drift, power frequency interference and measurement noise on subsequent processing;

Step 2: Processing feature point detection of the pre-processed ECG signal $x_2(i)$ to determine a feature point position and a QRS range, and obtaining an estimated ideal ECG signal by nonlinear transformation; first, processing feature point detection of the pre-processed ECG signal to determine a feature point position and a QRS range; secondly, filtering the pre-processed ECG signal obtained after processing step 1 by using two low-pass filters of different filtering frequencies respectively; then subtracting these two filtering results to obtain a difference signal, and searching for a first zero-crossing position before and after each feature point position of the difference signal; thereafter, substituting a time range contained in the first zero-crossing position before and after each feature point position by the filtering result with a higher filter frequency of the above two different filtering frequencies, and substituting other parts by the filtering result with a lower filter frequency of the above two different filtering frequencies to obtain a complex signal; finally, processing low-pass filtering for the complex signal to obtain an estimated ideal ECG signal;

Step 3: Based on the pre-processed ECG signal, the feature point position and the estimated ideal ECG signal, using a spline interpolation technique to obtain an accurate estimated ideal ECG signal; First performing subtraction between the pre-processed ECG signal obtained from the step 1 and the estimated ideal ECG signal obtained from the step 2 to obtain an error signal, and searching for a zero-crossing position of the error signal; then, at the zero-crossing position of the error signal obtained after searching and the feature point position obtained from the step 2, taking a spline weight as 1, and others as 0; finally, based on the estimated ideal ECG signal obtained from the step 1 and the spline weight obtained, using cubic smoothing splines to obtain an accurate estimated ideal ECG signal;

Step 4: Performing subtraction between the pre-processed ECG signal obtained from the step 1 and the accurate estimated ideal ECG signal obtained from the step 3, filtering a subtraction result by a band pass filter to obtain a filtered result; based on the filtered result and the QRS range obtained from the step 2, obtaining an abnormal potential in the QRS by moving standard deviation analysis technique;

Step 5: Processing credibility evaluation on the obtained abnormal potential in the QRS; Evaluating a credibility of the abnormal potential in the QRS obtained in step 4 by using a standard deviation analysis method, and determining whether the abnormal potential in the QRS obtained from the step 4 is credible, and outputting an evaluation result.

2. The method of accurately extracting abnormal potential in QRS according to claim 1, characterized in that, the step 2, specifically, is:

(1) Using $x_2(i)$ to process ECG feature point detection to obtain the QRS range, a starting position $QRS_b$, an ending position $QRS_e$ and a ECG feature point position $p(j)$, the number of feature points is M, J=1, 2, ..., M, The ECG feature points includes at least a QRS starting point, a QRS ending point, and Q, R, S waveform peak points;

(2) Filtering $x_2(i)$ by a higher frequency low-pass filter to obtain $x_h$,i, $f_h$ refers to a filter frequency of the low-pass filter, 100 Hz≤$f_h$≤200 Hz;

(3) Filtering $x_2(l)$ by a lower frequency low-pass filter to obtain $x_l(i)$, $f_l$ refers to a filter frequency of the low-pass filter, 40 Hz≤$f_l$≤80 Hz;

(4) calculating the difference signal $x_d(i)$ by formula (3):

$$x_d(i)=x_h(i)-x_l(i), \quad (3)$$

Wherein $x_h(i)$ is a filter result of $x_2(i)$ by the higher frequency low-pass filter, $x_l(i)$ is a filter result of $x_2(i)$ by the lower frequency low-pass filter;

(5) Based on the signal $x_d(i)$, searching the difference signal $x_d(i)$ for each ECG feature point time position $p(j)$, j=1, 2, ..., M, at backward and forward direction respectively to obtain a front and a back first zero crossing point respectively, then obtaining the corresponding time position $p_b(j)$ and $p_f(j)$ respectively;

(6) constructing a point set se(j) according to $p_b(j)$ and $p_f(j)$:

$$set(j)=\{p_b(j), p_b(j)+1, \ldots, p_f(j)-1, p_f(j)\}, \quad (4)$$

Based on this, construct $Set_h$:

$$set_h=\{set(1), set(2), \ldots, set(M)\}, \quad (5)$$

Based on $set_h$, synthesize a complex signal $x_s(i)$ by formula (6):

$$x_s(i) = \begin{cases} x_h(i), & i \in set_h \\ x_l(i), & i \notin set_h \end{cases}, \quad (6)$$

(7) Processing low-pass filtering of $x_s(i)$ to obtain estimated ideal ECG signal $x_3(i)$, $f_3$ refers to a filter frequency of the low-pass filter, 100 Hz≤$f_3$≤200 Hz.

3. The method of accurately extracting abnormal potential in QRS according to claim 1, characterized in that, the step 3, specifically, is:

(1) Calculating the error signal $x_e(i)$ by equation (7):

$$x_e(i)=x_2(i)-x_3(i), \quad (7)$$

$X_3(i)$ is the estimated ideal ECG signal;

(2) calculate the spline weight WO by equation (8):

$$w(i) = \begin{cases} 1, & i \text{ is the zero-crossing point of } p(i) \text{ or } x_e(i) \\ 0, & \text{others} \end{cases}, \quad (8)$$

(3) Based on the estimated ideal ECG signal 1 $x_3(i)$ and the spline weight w(i), using the three-order smooth splines to obtain an accurately estimated ideal ECG signal $x_4(i)$.

4. The method of accurately extracting abnormal potential in QRS according to claim 1, characterized in that, the step 4, specifically, is:

(1) calculate the difference signal e(i) by equation (9):

$$e(i)=x_2(i)-x_4(i) \quad (9)$$

$x_4(i)$ is the accurately estimated ideal ECG signal;

(2) Bandpass filter e(i) to obtain a signal y(i) which contains an abnormal potential in the QRS to be extracted, the bandpass filter bandwidth is selected according to specific needs;

(3) calculate a moving window variance msd(i) for the signal y(i), and calculate msd(i) by equation (10):

$$msd(i) = \quad (10)$$

$$\begin{aligned} & \frac{1}{2k+1}\left(\sum_{j=-k}^{k} y^2(i+j) - \frac{1}{2k+1}\left(\sum_{j=-k}^{j=k} y(i+j)\right)^2\right)^{\frac{1}{2}}, & k \leq i \leq N-k \\ & msd(k), & i < k \\ & msd(N-k), & i > N-k \end{aligned}$$

Wherein a window length is 2k+1, and k ranges from 2 ms~5 ms, and a calculated result of msd(i) is k=2 ms;

(4) calculate a reference MSD value $ref_{msd}$, define an interval of 100 ms before a starting position $QRS_b$ to $QRS_b$ at the QRS is as a reference interval, first calculate a mean value $ref\_msd_{mean}$ of msd(i) in the reference interval and a standard deviation $ref\_msd_{std}$, then calculate a $ref_{msd}$ by equation (11):

$$ref_{msd}=ref\_msd_{mean}+\alpha*ref\_msd_{std}, \quad (11)$$

wherein α is generally choose to be greater than 2;

(5) determine a starting position $AIQP_b$ of AIQPs based on $ref_{msd}$, the specific method is: starting a forward search from the QRS starting position $QRS_b$, and stopping the search if a duration of msd (j)>$ref_{msd}$ is greater than or equal to a preset constant m, wherein a position at this time is set as $t_b$, calculate the starting position of $AIQP_b$ of AIQPs by formula (12):

$$AIQP_b=t_b-M-k, \quad (12)$$

Wherein m is generally 5 ms; if the ending position $QRS_e$ of QRS is searched, then $AIQP_b$=0 and stopping the search;

(6) determine whether $AIQP_b$ is searched, if $AIQP_b$ is equal to 0, then exit and return a failure flag, otherwise continue;
(7) determine an ending position $AIQP_e$ of AIQPs based on $ref_{msd}$, wherein the specific method is: starting a backward search from approximately 50 ms after the QRS ending position $QRS_e$, if a duration of msd(i)>$ref_{msd}$ is greater than or equal to m, stopping the search, and the position at this time is set as $t_e$, calculate the ending position of $AIQP_b$ of AIQPs by formula (13):

$$AIQP_e = t_e + m + k, \qquad (13)$$

If the starting position $AIQP_b$ of AIQPs is searched, then $AIQP_e=0$ and stopping the search, determine whether $AIQP_e$ is searched, if $AIQP_e$ is equal to 0, then exit and return a failure flag, otherwise continue;
(8) extract abnormal potential AIQP(i) of QRS, which is calculated according to formula (14):

$$AIQP(i) = \begin{cases} y(i), & AIQP_b \le i \le AIQP_e \\ 0, & others \end{cases}, \qquad (14)$$

Wherein $AIQP_b$ is the starting position of AIQPs obtained by searching, $AIQP_e$ is the ending position of AIQPs obtained by searching.

5. The method of accurately extracting abnormal potential in QRS according to claim 1, characterized in that, the step 5, specifically, is:
(1) calculate the standard deviation of the reference interval $ref_{std}$ and the standard deviation of QRS region $QRS_{std}$, $ref_{msd}$ is standard deviation of the reference interval y(i), $QRS_{std}$ is the standard deviation of the y(i) in the interval from the QRS starting position $QRS_b$ to the QRS ending position $QRS_e$;
Determine the credibility of the extraction result, which is calculated by formula (15):

$$\text{credibility} = \begin{cases} 1, & QRS_{std} \ge \beta * ref_{std} \text{ or } ref_{std} > 5 \ \mu V \\ 0, & others \end{cases}, \qquad (15)$$

Wherein $\beta>1$, the specific selection can be determined according to the actual situation;
If the credibility is equal to 0, then return a failure flag, otherwise return a success flag and at the same time return the extracted abnormal potential AIQP(i) in the QRS.

\* \* \* \* \*